United States Patent [19]

Lattner et al.

[11] Patent Number: 5,292,985
[45] Date of Patent: Mar. 8, 1994

[54] MULTI-STAGE OLEFIN ISOMERIZATION

[75] Inventors: James R. Lattner, Seabrook; Robert S. Smith, Houston, both of Tex.

[73] Assignee: Exxon Chemical Patents, Inc., Linden, N.J.

[21] Appl. No.: 699,545

[22] Filed: May 14, 1991

[51] Int. Cl.$^5$ .................................................. C07C 5/22
[52] U.S. Cl. .................................... 585/671; 585/664; 502/344
[58] Field of Search ..................... 585/671, 926, 664

[56] References Cited

U.S. PATENT DOCUMENTS

| | | | |
|---|---|---|---|
| 2,337,409 | 12/1943 | Sensel | 585/926 |
| 2,740,820 | 4/1956 | Wilson et al. | 260/683.2 |
| 3,347,944 | 10/1967 | Fritz et al. | 260/666 |
| 3,405,196 | 4/1967 | Wolff | 260/683.2 |
| 3,577,473 | 5/1971 | Nagase | 260/666 |
| 3,577,473 | 5/1971 | Nagase et al. | 260/666 |
| 3,808,152 | 4/1974 | Nagase et al. | 252/463 |
| 3,897,509 | 7/1975 | Nagase et al. | 260/666 |
| 3,928,485 | 12/1975 | Nagase et al. | 260/680 |
| 4,205,192 | 5/1980 | Harada | 585/363 |
| 4,229,610 | 10/1980 | Myers | 585/664 |
| 4,675,307 | 6/1987 | Taniguchi et al. | 502/306 |
| 4,720,601 | 1/1988 | Suzukamo et al. | 585/377 |
| 4,727,204 | 2/1988 | Suzukamo et al. | 585/377 |

Primary Examiner—Asok Pal
Assistant Examiner—P. Achutamurthy
Attorney, Agent, or Firm—Linda K. Russell

[57] ABSTRACT

A multi-stage process for isomerizing olefin compounds to the corresponding product olefin compounds is provided. The isomerization catalyst comprises an oxygen treated mixture of an alkali metal on a calcined support. The multi-stage process is particularly useful for isomerizing 5-vinyl-2-norbornene to 5-ethylidiene-2-norbornene. The catalyst is very active and highly selective and resistant to catalyst poisons. The process contacts the catalyst with an isomerizable olefin in at least two reaction stages to yield the corresponding product olefin compound. The reaction stages differ in temperature, catalyst activity or both.

7 Claims, 4 Drawing Sheets

MULTI-STAGE OLEFIN ISOMERIZATION

BACKGROUND OF THE INVENTION

1. Field of the Invention

The present invention relates to a multi-stage process for isomerizing olefins. This invention is particularly well-suited for isomerizing an alkenyl bridged ring compound to the corresponding alkylidene bridged ring compound. The advantages of the multi-stage process are provided by use of a highly active and highly selective isomerization catalyst. The process of the invention is particularly useful for isomerizing 5-vinyl-2-norbornene (hereinafter "VNB") to 5-ethylidene-2-norbornene (hereinafter "ENB"), which is used commercially in the production of elastomeric polymers and synthetic rubber. The highly active isomerization catalyst is prepared by adding an alkali metal to alumina and then activating the mixture by careful oxidation of the alkali metal.

2. Description of the Prior Art

Isomerization of olefins is well-known in the art. An incentive for isomerization arises when the olefinic double bond in the starting isomerizable olefin must be moved to a different position in order to provide a properly reactive olefin. For instance, it is known to isomerize pentene-1 to pentene-2 so that pentene-2 may be used in the catalytic alkylation of an isoparaffin. The resulting alkylate is useful as an additive to enhance octane in gasoline. Also, the double bond in an olefinic intermediate compound may need to be shifted in position in order to continue synthesis of the desired final chemical product.

Isomerization is also used to provide olefins necessary for polymerization. One such olefin is ENB. The use of ENB as a monomer in the production of rubbery polymers is well known. ENB may be produced by reacting 1,3-butadiene and cyclopentadiene in an addition reaction commonly known as a Diels-Alder reaction, yielding VNB which is then catalytically isomerized to ENB.

Known isomerization catalysts include liquid bases, such as mixtures of alkali metal hydroxides and aprotic organic solvents, mixtures of alkali metal amides and amines, and mixtures of organic alkali metal compounds and aliphatic amines. Unfortunately, the catalytic activity of the liquid bases is relatively low, and therefore a large amount of these expensive catalysts must be used. Also, recovery of the catalyst from the reaction mixture is very difficult, requires complicated separation and recovery steps and consumes a large amount of energy.

Solid isomerization catalysts are also known, for example, alkali metals carried on large surface area anhydrous supports such as activated carbon, silica gel, alumina and the like. These solid catalysts are difficult to handle because they may ignite and lose activity on contact with oxygen. Also, the isomerization performance of these solid catalysts is poor, because conversion and selectivity are low.

U.S. Pat. No. 3,897,509 discloses that heating an alkali metal, an alkali metal hydroxide and alumina yields an alkali catalyst composition which is described to be stable on exposure to air and water and active in various chemical reactions. Particularly the catalyst is said to be useful in the isomerization of alkenyl bridged ring compounds to the corresponding alkylidene bridged ring compounds. Thus, it is useful for the production of alkylidene bridged ring compounds such as ENB which is valuable in the production of synthetic rubber.

The preferred method of forming the catalyst of U.S. Pat. No. 3,897,509 is by heating and mixing an alkali metal, an alkali metal hydroxide and alumina at a temperature higher than the melting point of the alkali metal; however, the catalyst may also be prepared without the use of an alkali metal hydroxide if the starting alumina contains water.

U.S. Pat. No. 3,405,196 discloses a process in which a terminal olefin is converted to an internal olefin in the presence of a supported alkali-metal catalyst that has been pretreated with an oxygen containing gas such as nitrous oxide. The catalyst used contains an alkali metal dispersed on a high-surface area, substantially inert support. The alkali metal may be selected from sodium, potassium, rubidium and cesium. The desired catalyst support material is a high surface area, large pore, and slightly acidic alumina. The catalyst is primarily used to convert 1-pentene to 2-pentene and 1-butene to 2-butene and is not used to isomerize an alkenyl bridged ring compound to an alkylidene bridged ring compound.

Many of these prior art catalysts will react violently with water and suffer from poor conversion activity. The catalysts also deactivate on contact with catalyst poisons. These and other shortcomings of the prior art are overcome by the present invention, and a new multi-stage process for isomerizing olefins is provided.

SUMMARY OF THE INVENTION

The present invention relates to a multi-stage process for isomerizing olefins, particularly for isomerizing alkenyl bridged ring compounds to the corresponding alkylidene bridged ring compounds. A highly active and highly selective isomerization catalyst prepared as described herein provides resistance to catalyst poisons and therefore provides the advantages realized by the multi-stage process. The process of the invention is particularly useful for isomerizing 5-vinyl-2-norbornene an alkenyl bridged ring compound, to 5-ethylidene-2-norbornene, an alkylidene bridged ring compound which is used commercially as the diene monomer in ethylene-propylene-diene monomer rubber (EPDM). The highly active isomerization catalyst is prepared by adding an alkali metal to a properly prepared calcined support material followed by careful oxidation of the alkali metal.

The inventive multi-stage process for isomerizing olefins comprises contacting the olefin to be isomerized with the isomerization catalyst in sequential stages differing by temperature, catalyst activity or both. One particular embodiment of the multi-stage process comprises contacting a chemical plant stream comprising an isomerizable olefin with an activated catalyst in sequential stages differing by temperature, catalyst activity or both. The advantages of the multi-stage process are especially apparent when the chemical plant stream comprises an isomerization catalyst poison. The activated catalyst is prepared by heating a support material to form a calcined support material, contacting the calcined support material with an alkali metal to form a catalyst precursor mixture of alkali metal and calcined support material, and contacting the mixture with an activating gas.

One particular aspect of the invention is a process for isomerizing an olefin comprising:

(a) passing a fluid stream initially comprising an isomerizable olefin sequentially through a series of reaction zones from a first reaction zone to a last reaction zone;
(b) contacting the fluid stream with an isomerization catalyst in each reaction zone;
wherein the isomerization catalyst comprises an oxygen treated mixture of an alkali metal supported on a calcined support material and wherein the temperature of the first reaction zone is higher than the temperature of the last reaction zone.

Another aspect of the invention is a multi-stage process for isomerizing a stream comprising an isomerizable olefin which comprises:
(a) introducing a stream comprising an isomerizable olefin to a first reaction zone and contacting the stream with an isomerization catalyst therein whereby some of the isomerizable olefin is converted to product olefin;
(b) removing from the first reaction zone a first outlet fluid stream comprising unconverted isomerizable olefin;
(c) removing from the first reaction zone a first outlet catalyst stream comprising isomerization catalyst from the first reaction zone;
(d) introducing the first outlet fluid stream to a second reaction zone and contacting the first outlet fluid stream with an isomerization catalyst therein whereby some of the isomerizable olefin is converted to product olefin;
(e) removing from the second reaction zone a second outlet fluid stream;
(f) removing from the second reaction zone a second outlet catalyst stream comprising isomerization catalyst from the second reaction zone; and
(g) introducing the second outlet catalyst stream to the first reaction zone.

Features of this invention are the high level of conversion of the isomerizable olefin, the high selectivity to the desired product olefin, efficient catalyst utilization and efficient removal of and resistance to catalyst poisons. Another feature of this invention is the stability of the catalyst used to effect isomerization and the economy of the process for isomerizing olefins. This is achieved by discovery of a catalyst uniquely resistant to common impurities found in isomerizable olefin feedstock streams. Accordingly, these and other features of this invention will become apparent from the following detailed description, wherein reference is made to the Figures in the accompanying drawings.

IN THE DRAWINGS

DETAILED DESCRIPTION OF THE INVENTION

Figure 1:
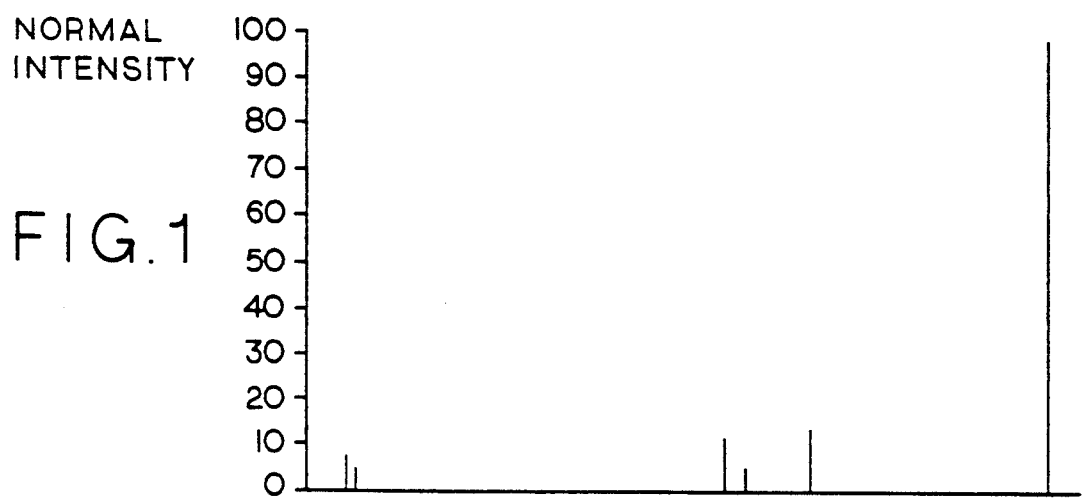
FIG. 1 is an X-ray diffraction pattern for alumina.

The olefin undergoing isomerization according to this invention is termed the isomerizable olefin. During olefin isomerization, the olefinic double bond shifts from one position to another position. Although it is theoretically possible to shift the olefinic double bond to any position available between two carbon atoms of the olefinic molecule, in reality only certain shifts are favored. The isomerizable olefins discussed herein are olefins with the double bond in a position that is unfavored at equilibrium over the particular catalyst. Therefore, the double bond will tend to shift its position when the isomerizable olefin contacts a catalyst with isomerization activity. The resulting product is termed the product olefin.

Specific examples of isomerizable olefins and the corresponding product olefin are listed in Table I below.

TABLE I

| Isomerizable Olefin | Product Olefin |
|---|---|
| 1-butene | 2-butene |
| 1-pentene | 2-pentene |
| 1-hexene | 2-hexene, 3-hexene |
| 2-hexene | 3-hexene |
| VNB | ENB |

The multi-stage process is particularly useful for isomerizing alkenyl bridged ring compounds to alkylidene bridged ring compounds. Alkenyl bridged ring compounds may be produced by a Diels-Alder reaction.

The Diels-Alder reaction is an additive reaction of an olefin with a conjugated diene. The Diels-Alder reaction proceeds without a catalyst at temperatures ranging from about 50° to 250° C. Alkenyl bridged ring compounds may be produced by the Diels-Alder reaction of cyclodienes with aliphatic dienes. VNB is produced by the Diels-Alder reaction of 1,3-butadiene with cyclopentadiene.

The conditions necessary to bring about the Diels-Alder reaction of 1,3-butadiene with cyclopentadiene are well known in the art. In particular, butadiene may be contacted with cyclopentadiene in the liquid phase at temperatures of from 100° to 200° C. and a pressure of from 150 to 300 lbs/square inch. It is not necessary to use a catalyst to advance the Diels-Alder reaction. The reaction is generally completed in 0.1 to 100 hours and is usually conducted under an inert atmosphere. Preferably, the reaction may be conducted in a liquid state most preferably in a liquid-full reaction vessel.

The preferred reaction occurs between 1,3-butadiene and cyclopentadiene, however, undesirable polymerization reactions may also occur. For example, 1,3-butadiene monomers may react with other 1,3-butadiene monomers to form butadiene homopolymers. Similar polymerization reactions may occur between cyclopentadiene monomers, and between 1,3-butadiene and cyclopentadiene. Certain compounds are known which suppress or inhibit the undesired polymerization reactions. Any one or combination of these inhibitor compounds may be added to the reactants in order to produce more VNB from the same amount of starting material and to avoid plugging certain parts of the reaction apparatus with the high molecular weight polymers which might otherwise be formed. Many inhibitor compounds are known in the art including but not limited to 2,6-di-t- butyl-p-cresol, diphenylnitrosamine, and N-substituted p-phenylenediamines.

The Diels-Alder reaction product mixture may be passed directly to the isomerization process, however, it is commercially preferred to purify the reaction product stream may be purified by fractional distillation under increased pressure, atmospheric pressure or preferably at reduced pressures. Extractive distillation techniques may also be used and some of the known extractive distillation solvents are acetonitrile, water, sulfolane and N-methylpyrrolidone (NMP). The reaction product may also be purified by extraction, by extraction followed by distillation, or by crystallization. The Diels-Alder reaction product or preferably the purified VNB is then isomerized in order to convert VNB to ENB. As mentioned above, although the multi-stage process is particularly useful for isomerizing VNB to ENB, the process is also useful for isomerizing other isomerizable olefins.

The stream to be isomerized may be 90% or more by volume of the isomerizable olefin or the stream may be diluted with a solvent that is inert during the isomerization process. Appropriate solvents include aliphatic compounds such as hexane, heptane, octane and isooctane, and aromatic compounds such as benzene, toluene, xylene and ethylbenzene. Many other solvents are acceptable and within the scope of the invention; however, certain types of compounds are isomerization catalyst poisons and should not be used as solvents. These poisons include water, alcohols, acid compounds and conjugated diene compounds.

The isomerization catalyst utilized in the inventive process is comprised of an alkali metal on a calcined support material, the combination being further treated with a gas containing oxygen. The alkali metal may be selected from the group comprising lithium, sodium, potassium, rubidium, cesium and mixtures thereof. The alkali metal consists essentially of the metal in its elemental state, for example, if potassium is the alkali metal, it should be added as pure potassium and not in combination with another element, i.e., potassium hydroxide. Sodium is the preferred alkali metal. The catalyst may be prepared by dispersing 1-40 wt % alkali metal on a calcined support material at temperatures of from 100°-600° C. under an atmosphere of dry, inert gas. The alkali metal dispersed on the support material is then subjected to oxidation by contact with a gas having an oxygen content of 0.1 to 25 mole % at temperatures of 0°-300° C.

The material of the support upon which the alkali metal should be dispersed may be any normally solid material which has high surface area and large pores. The support material should also remain in the solid state at the elevated temperatures required during calcination and alkali metal dispersion. Preferably, the support material has a surface area ranging from about 5 to 1,000 square meters per gram ($m^2/g$) more preferably from about 20 to 600 $m^2/g$ and most preferably from about 100 to 200 $m^2/g$. In fact, some surprisingly active catalysts have been prepared from support material with a surface area of about 180 $m^2/g$. The pore size of the support material may range from about 5 to 1,000 Angstroms more preferably from 10 to 300 Angstroms and most preferably from 10 to 100 Angstroms. The support material used for preparing the catalyst may be in powder, pelletized, or extruded form. The support material should be calcined under a dry atmosphere, and it should be free of water and entrained oxygen after calcination.

Alumina, silica, and oxides of metals of Groups 3A, 4A and 4B of the Periodic Table may be used as the support material. The Periodic Table referred to is the table as reproduced in the CRC Handbook of Chemistry and Physics, 53rd edition. Other examples of specific support materials include carbon, graphite, magnesia, titania, zirconia, calcium oxide, magnesium oxide, sodium oxide and barium oxide. Alumina is the preferred support material and in a most preferred embodiment, the support material consists essentially of alumina. Alumina consists of mostly $Al_2O_3$ and small amounts of $Na_2O$, $SiO_2$ and $Fe_2O_3$. The form of alumina utilized in the most preferred embodiment is gamma alumina.

The support should be calcined prior to contact with the alkali metal. Calcination is effected by heating the support material at temperatures of from 100° to 1,000° C., more preferably from about 300° to about 800° C. and most preferably from about 400° to about 600° C. The calcination may be conducted at atmospheric pressure or higher, however, reduced pressures are preferred. Preferably an inert gas is purged through the calcination vessel in order to sweep away any water or oxygen molecules which may be driven off from the support material by the heat. The calcination should last for from about 0.1 to 100 hours preferably from about 1 to 20 hours. The heat of calcination drives water from the support material, and provides an essentially dry support material. After calcination, the support material should be kept under a dry atmosphere so that water does not become associated with the support material.

The catalytic combination of alkali metal and support material is prepared by first contacting the calcined support material with the alkali metal under a dry, inert, oxygen free atmosphere thus forming a catalyst precursor mixture. The alkali metal is preferably in the molten state during at least a portion of the contact and the contact occurs by physically blending the calcined support material with the alkali metal under the dry, inert, oxygen free atmosphere. In the most preferred embodiment, the catalyst precursor mixture consists essentially of the alkali metal and the support material.

The alkali metal may be initially contacted with the calcined support material while the alkali metal is in the solid, liquid or gaseous state. Usually the initial contact occurs at a temperature of from about 0° to about 500° C., preferably from about 10° to about 40° C. under an inert atmosphere. If the alkali metal is in the solid state when initially contacted with the support material, the temperature of the mixture should be raised enough to melt the alkali metal, and the mixture should be stirred for initial dispersion of the alkali metal on the support material. Gasses such as nitrogen, argon, helium and krypton will provide an inert atmosphere. The resulting mixture is then heated to a temperature of from about 100° to about 600° C. preferably about 300° to about 400° C. under constant agitation.

The mixing agitation may be discontinued after the alkali metal is roughly dispersed on the support material, however, it is preferable to continue mixing until the alkali metal is evenly distributed on the surface of the calcined support material. In the case of a mixture of sodium on alumina, a visual indication of a blue black evenly distributed color over the surface of the alumina indicates uniform distribution of sodium. If large amounts of materials are to be mixed or slow mixing speeds are used, complete uniform dispersion will take longer, however, mixing is often complete within about two hours when a rotary mixer is used to produce 100 grams of catalyst.

The amount of alkali metal which should be distributed upon the calcined support material is in the range of from about 1 to about 40 wt % based upon the total weight of the mixture comprising both alkali metal and calcined support material. Preferably the range of alkali metal is from about 5 to about 20 wt % and most preferably from about 10 to about 15 wt %.

After the alkali metal has been dispersed upon the calcined support material to form a catalyst precursor mixture, the mixture should be contacted with an activating gas containing oxygen. Since a violent reaction between the alkali metal and oxygen will occur if oxygen is added too quickly, care should be taken to avoid exposing the mixture to excessive oxygen initially. If the temperature of the mixture exceeds about 300° C. during the activation, the rate of oxygen contact with the mixture should be reduced. The rate of oxygen contact may be reduced by lowering the flow rate of oxygen containing gas or by reducing the concentration of oxygen in the oxygen containing gas. Some inert gas flow should be maintained in order to reduce the temperature of the catalyst mixture to a safe level. Alternatively, pure oxygen at reduced pressure may be used as the activating gas.

The catalyst mixture may be contacted with the activating gas at a temperature within the range of from about 0° to about 300° C. preferably about 20° to 150° C. and most preferably about 25° to about 50° C. The catalyst mixture may be agitated while the contact with the activating gas occurs. In an alternative method of catalyst preparation, the catalyst mixture is contacted with the activating gas at high temperatures. Typically, the temperatures should be about 55° to about 300° C., preferably about 65° to about 300° C. and most preferably about 100° to about 300° C.

The activating gas may comprise a single type of gaseous compound containing oxygen or a mixture of an inert gas with another gas containing oxygen. Examples of activating gases include nitric oxide, nitrous oxide, sulfur dioxide, dry air, ozone, and mixtures of oxygen with nitrogen, helium, argon, krypton, xenon, or radon. Mixtures of these gases or mixtures may also be used. In a preferred embodiment a mixture of oxygen ($O_2$) in nitrogen ($N_2$) may be used as the activating gas. The amount of oxygen in the activating gas should be from about 0.1 to about 25 mole %. Preferably the amount of oxygen in the activating gas mixture is from about 2 to about 10 mole % and most preferably about 5 mole %. If pure oxygen (100 mole % $O_2$) is used as the activating gas, the pressure should be reduced to between about 0.001 and 0.25 atmosphere.

If oxygen is only part of an oxygen containing molecule, such as NO or $NO_2$, the oxygen content of the gas is calculated by dividing the atomic weight of oxygen in the molecule by the molecular weight of the gas.

The contact between the oxygen containing gas and the mixture may be continued until all of the alkali metal has been oxidized; however, it is preferable to stop the contact when the oxygen to alkali metal atomic ratio is within the range of from about 0.01 to about 2.0 atoms of oxygen per atom of alkali metal. Preferably the ratio is within the range of from about 0.2 to 0.5 atoms of oxygen per atom of alkali metal.

The catalyst prepared as described above will have activity to isomerize olefins, such as VNB, into product olefins, such as ENB.

Any isomerizable olefin may be isomerized by the multi-stage process, but alkenyl bridged ring compounds are particularly well suited to isomerization by the catalyst. Alkenyl bridged ring compounds are of the general formula (I):

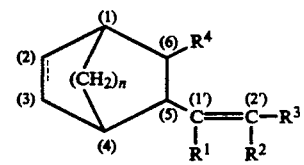

wherein $R^1$, $R^2$ and $R^3$ are each hydrogen or alkyl having 1 to 8 carbon atoms, $R^4$ is hydrogen or alkyl having 1 to 4 carbon atoms, and n is 1 or 2 and wherein a double bond may be present at the place between the 2- and 3-positions as indicated by the dotted line.

Specific examples of some alkenyl bridged ring compounds are:
5-vinylbicyclo[2,2,1]heptane;
5-(1'-propenyl)-bicyclo[2,2,1]heptane;
5-(1'-butenyl)-bicyclo[2,2,1]heptane;
5-isopropenylbicyclo[2,2,1]heptane;
5-(2'-methyl-1'-propenyl)bicyclo[2,2,1]heptane;
6-methyl-5vinylbicyclo[2,2,1]heptane;
6-methyl-5-isopropenyl[bicyclo[2,2,1]heptane;
6-ethyl-5-vinylbicyclo[2,2,1]heptane;
5-vinylbicyclo[2,2,1]hepta-2-ene;
5-(1'-propenyl)-bicyclo[2,2,1]hepta-2-ene;
5-(1'-butenyl)-bicyclo[2,2,1]hepta-2-ene;
5-isopropenylbicyclo[2,2,1]hepta-2-ene;
5-(2'-methyl-1-propenyl)-bicyclo[2,2,1]hepta-2-ene;
5-(1'-octenyl)-bicyclo[2,2,1]hepta-2-ene;
6-methyl-5-vinylbicyclo[2,2,1]hepta-2-ene;
6-methyl-5-isopropenylbicyclo[2,2,1]hepta-2-ene;
6-ethyl-5-vinylbicyclo[2,2,1]hepta-2-ene;
5-vinylbicyclo[2,2,1]octane;
5-(1'-propenyl)-bicyclo[2,2,2]octane;
5-isopropenylbicyclo[2,2,2]octane;
5-(1'-butenyl)-bicyclo[2,2,2]octane;
6-methyl-5-vinylbicyclo[2,2,2]octane;
6-methyl-5-isopropenylbicyclo[2,2,2]octane;
5-vinylbicyclo[2,2,2]octane;
5-(1'-propenyl)-bicyclo[2,2,2]octa-2-ene;
5-isopropenylbicyclo[2,2,2]octa-2-ene;
5-(1'-butenyl)-bicyclo[2,2,2]octa-2-ene;
5-(2'-methyl-1'-propenyl)-bicyclo[2,2,2]octa-2-ene;
6-methyl-5-vinylbicyclo[2,2,2]octa-2-ene; and
6-methyl-5-isopropenylbicyclo[2,2,2]octa-2-ene.

The compounds represented by formula I can be produced by subjecting a cyclic diene such as cyclopentadiene or cyclohexadiene and an aliphatic 1,3-diene to a Diels-Alder reaction or by subjecting the corresponding bridged ring compound bearing a hydroxyl group at the 1'- or 2'-position to dehydration.

Isomerization of an alkenyl bridged ring compound shifts the double bond from 1'-2' position to the 5-1' position of formula I thereby forming the alkylidene bridged ring compound.

The isomerization is effected by contacting an isomerizable olefin, for example, a VNB stream, with the catalyst at temperatures of from about −50° to about 200° C. Preferred temperatures of isomerization range from about 0° to about 150° C., most preferably from about 20° to about 100° C.; however, an initial contact temperature of at least 80°, preferably about 100° C., may be beneficial is the isomerizable olefin stream is contaminated with catalyst poisons such as cyclopentadiene. The high temperature multi-stage isomerization embodiment of the invention is particularly useful for isomerizing chemical plant streams comprising a substantial amount of isomerizable olefins, and further comprising isomerization catalyst poisoning compounds. This is because of the surprising and unexpected discovery that this particular catalyst is resistant to catalyst poisons. The catalyst is especially effective at higher temperature isomerization conditions as will be apparent below.

The amount of catalyst used is not critical, although the use of more catalyst will reduce the time necessary to bring about a given level of conversion at the same temperature. Generally the weight of alkali metal utilized per weight of isomerizable olefin ranges from 1 part alkali metal for 10,000 parts of isomerizable olefin to 1 part alkali metal for 50 parts of isomerizable olefin. In fixed bed processes, the weight average space velocity expressed in terms of weight of feed per hour divided by the weight of supported catalyst in the fixed bed should range between 0.1 to 500 $Hr^{-1}$.

The multi-stage isomerization process may be conducted at any pressure, however, pressures of from about 0 to about 100 psig are preferred. The reaction may be conducted in liquid phase or gas phase. Reaction time varies depending on the reaction temperature and the amount of catalyst used, but generally ranges from 5 minutes to 6 hours. The isomerization reaction is generally conducted in the absence of oxygen and water.

The multi-stage isomerization process utilizes at least two reaction stages that differ by either reaction stage temperature or catalyst activity or preferably both temperature and activity. The temperature of each reaction stage, for an overall multi-stage process conducted in a series of vessels, is the average temperature of the material in each corresponding vessel. If the multi-stage process is conducted in a single fixed bed of catalyst wherein the temperature varies continuously from one end of the bed to the other end, the bed may be effectively thought of as a series of stages. The temperature of one reaction stage from such a series is the weighted average temperature of the stage. Such a fixed bed arrangement may be arbitrarily divided into two hypothetical stages or an infinite number of hypothetical stages based on temperature differences between the hypothetical stages.

The multi-stage process must have at least two reaction stages. Where the reaction stages differ by temperature, it is preferable to add the isomerizable olefin such as an alkenyl bridged ring compound to the reaction stage with the highest temperature. Since the isomerization reaction occurs faster at higher temperature, addition of the isomerizable olefin to the highest temperature stage provides for rapid conversion of the isomerizable olefin to the product olefin. When an alkenyl bridged ring compound is the isomerizable olefin, the product olefin will be an alkylidene bridged ring compound, and specifically when VNB is the isomerizable olefin, the product olefin will be ENB.

Surprisingly, the catalyst has activity to convert catalyst poison compounds such as cyclopentadiene into compounds which are not catalyst poisons. The catalyst poison compounds are converted at any reaction temperature, but at higher temperatures the catalyst poison removal occurs faster. Therefore, a stream comprising an isomerizable olefin and a catalyst poison may be contacted with the highest temperature reaction stage first in order to quickly remove the catalyst poison in addition to isomerizing the olefin. This arrangement provides a further advantage in that catalyst poison compounds are quickly neutralized. Once the catalyst poison compounds in the stream have been converted or neutralized, the catalyst in the following reaction stage or stages is protected from deactivation by the catalyst poison compounds.

Figure 4:
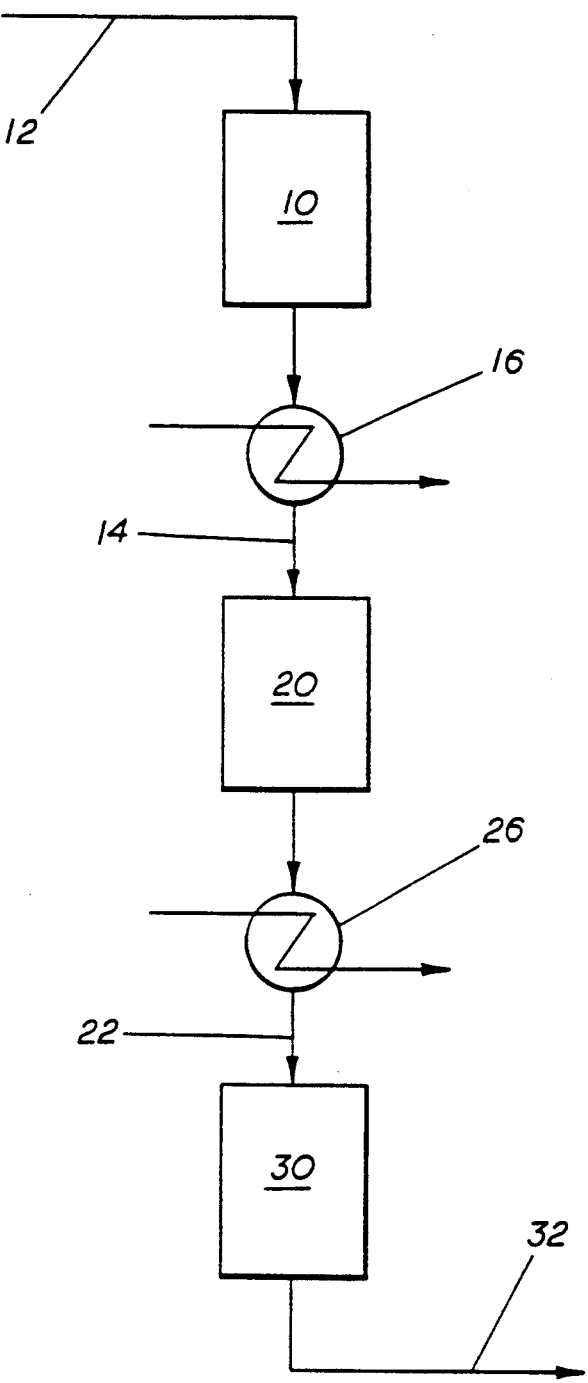
FIG. 4 is a block diagram of a 3-stage isomerization process.

In one embodiment of the invention, a fluid stream initially comprising an isomerizable olefin is passed through a series of at least three reaction zones and the temperature of each successive reaction zone, from a second reaction zone to the last reaction zone, is lower than the temperature of the prior reaction zone. This aspect of the invention may be better understood by reference to FIG. 4 which depicts a 3-stage process. A vessel 10 is provided, the outlet of which is connected to the inlet of vessel 20 by conduit 14. Conduit 14 may pass through a heat exchanger 16. Conduit 22 connects the outlet of vessel 20 with the inlet of vessel 30, and may pass through a heat exchanger 26. Conduit 32 is connected to the outlet of vessel 30.

In operation, vessels 10, 20 and 30 are provided with an isomerization catalyst as described above. The catalyst may be provided in a fixed bed arrangement or the catalyst may be present in the form of a slurry. If the catalyst is in the form of a slurry, each of the vessels 10, 20 and 30 should be provided with a means of agitation for maintaining the catalyst in a slurry to prevent the solid catalyst particles from settling to the bottom of the vessel. Vessels 10, 20 and 30 provide the first, second and third or last reaction zones respectively.

A stream comprising an isomerizable olefin such as an alkenyl bridged ring compound is introduced to vessel 10 through conduit 12. Vessel 10 provides a first-stage reaction zone wherein the isomerizable olefin contacts the isomerization catalyst and is at least partially converted to the corresponding product olefin compound. The temperature, pressure and reaction time within the first-stage reaction zone should be within the ranges set forth above.

A first outlet fluid stream is withdrawn from the first-stage reaction zone in vessel 10 and introduced to a second-stage reaction zone in vessel 20 through conduit 14. The first outlet fluid stream withdrawn from the first-stage reaction zone should not contain substantial amounts of solid catalyst. Means for substantially separating solid catalyst particles from a fluid stream are well known in the art and are therefore not discussed herein.

The second-stage reaction zone should be maintained at a temperature lower than the temperature of the first-stage reaction zone, but otherwise, the temperature, pressure and reaction time may vary within the limits set forth above. In order to maintain the temperature of the second-stage reaction zone lower than the temperature of the first-stage reaction zone, it may be necessary to cool the first outlet fluid stream. This cooling may be accomplished by passing the first outlet fluid stream through a heat exchanger 16 wherein heat flows from the first outlet fluid stream into a heat exchange fluid.

As noted above, the isomerization reaction proceeds at a faster rate at higher temperatures. Unfortunately, the isomerization equilibrium at higher temperatures may not favor complete conversion of the isomerizable olefin. Complete conversion is favored by equilibrium at lower temperatures. In the multi-stage process, the second-stage reaction zone is cooler than the first-stage reaction zone, and therefore the overall conversion of isomerizable olefins tends to be more complete.

The use of at least two reaction stages will provide the advantages described above. However, it may be desirable to use three or more reaction stages to provide more efficient catalyst usage. In the embodiment depicted by FIG. 4, a third-stage reaction zone is indicated by vessel 30. A second outlet fluid stream is withdrawn from the second-stage reaction zone and passed to the third-stage reaction zone. The second outlet fluid stream may be cooled by heat exchanger 26, if necessary, and the third-stage reaction zone should be maintained at a temperature lower than the temperature of the second-stage reaction zone. The temperature, pressure and reaction time should otherwise be within the limits set forth above. Additional reaction stages may be utilized in the same manner as the three reaction stages described above, for example, the fluid stream initially comprising an isomerizable olefin could be passed through a series of four sequential reaction zones.

Figure 5:
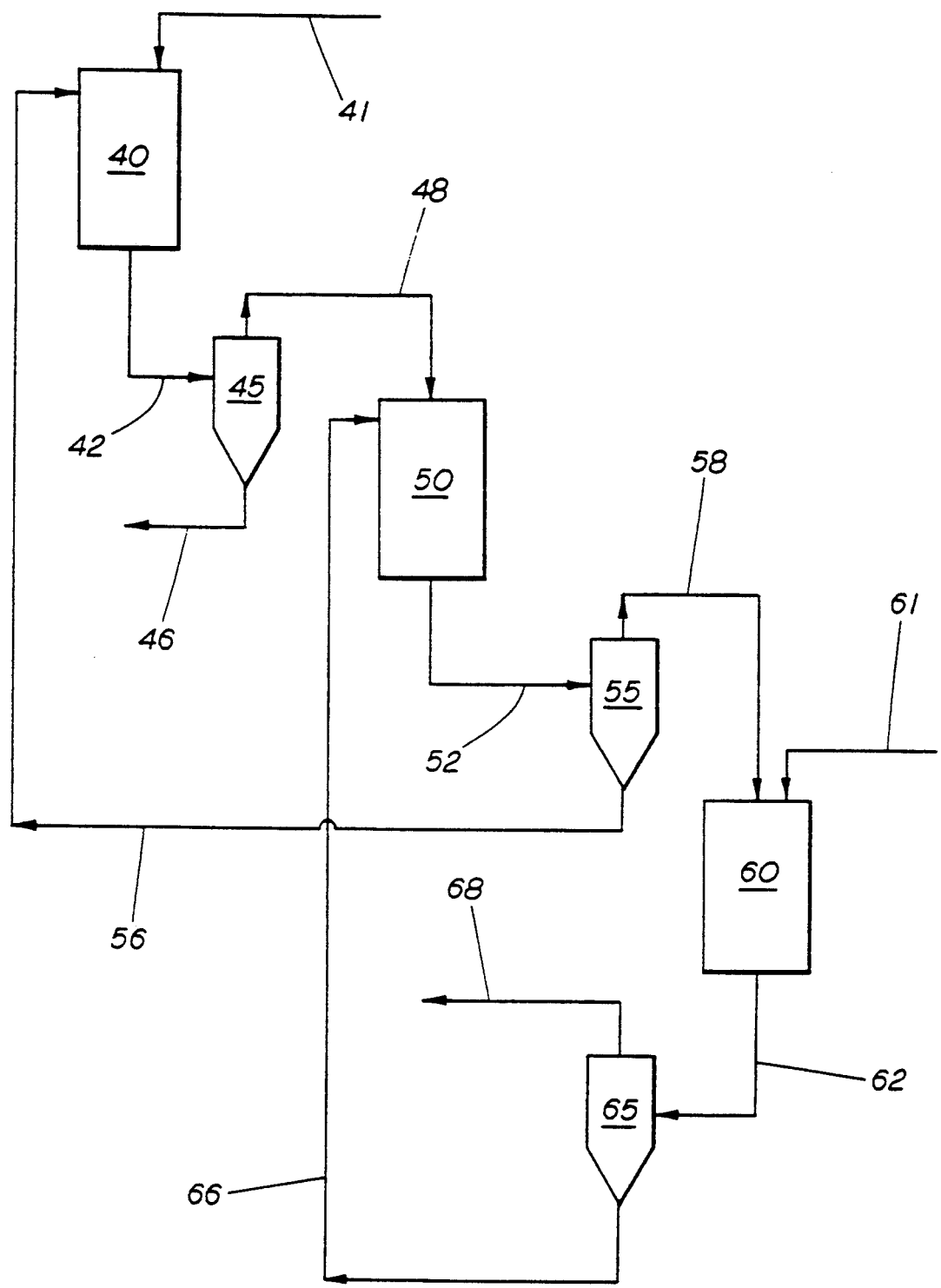
FIG. 5 is a block diagram of a 3-stage isomerization process wherein the catalyst is continuously transferred from stage to stage.

Another embodiment of the invention is depicted by FIG. 5 which shows a process wherein each stage may be maintained at the same or different temperature and the isomerization catalyst is transferred from stage to stage. In this embodiment, a first reaction zone is provided as by vessel 40. The inlet of vessel 40 is connected with a conduit 41. A fluid stream initially comprising an isomerizable olefin such as an alkenyl bridged ring compound may be introduced to the first reaction zone via conduit 41. The isomerization catalyst prepared as described above is also present in the first reaction zone thereby providing for contact between the fluid stream initially comprising the isomerizable olefin and the isomerization catalyst. This contact may occur at temperatures, pressure and reaction times within the limits set forth above.

The catalyst in the first reaction zone may be packed in a fixed bed thereby allowing the stream comprising the isomerizable olefins to trickle down over the catalyst particles. Since catalyst will be added and removed from the bed, means for adding catalysts and removing catalysts from the bed should be provided. Means for catalyst addition and removal from a fixed bed or a fluidized bed are well known by those of ordinary skill in the art of solid particle catalysis. Instead of a fixed bed or fluidized bed arrangement the catalyst may be slurried or stirred in the first reaction zone by providing a means of agitation of the fluid within the first reaction zone. The methods used to contact the isomerizable olefin with the catalyst are not critical and any method which will provide for contact between the catalyst and the isomerizable olefin will suffice.

The outlet of vessel 40 is connected to separator 45 through conduit 42. Conduit 42 provides for the removal of materials from the vessel 40 which comprise unreacted isomerizable olefin compounds, product olefin compounds and isomerization catalyst. These materials are then introduced to separator 45 which provides for separation of the solid catalyst particles from the other materials. Conduit 46 is connected to the catalyst outlet of separator 45 and provides for removal of the solid catalyst particles from the separator 45. These solid catalyst particles may be disposed of, regenerated and reused, or recycled back to the first reaction zone.

The invention further comprises a second reaction zone, for example vessel 50 which is connected to the fluid outlet of separator 45 through conduit 48. Fluid materials coming from the separator 45 comprise substantially all of the materials withdrawn from the first reaction zone except for the solid catalyst particles which have been removed through conduit 46. These fluid materials comprise any unreacted isomerizable olefin compounds and product olefin compounds. These fluid materials are then introduced to the second reaction zone.

The second reaction zone contains isomerization catalyst prepared as described above. The second reaction zone may be maintained at the same temperature or at a temperature lower than the outlet temperature for the first reaction zone. Otherwise, the temperature, pressure and reaction times should be within the limits set forth above. Contact between the isomerization catalyst and the materials which have been introduced through conduit 48 occurs in the second reaction zone thereby providing for further conversion of the isomerizable olefin compounds to the corresponding product olefin compounds.

Materials from the second reaction zone are moved from the outlet of vessel 50 and transferred to separator 55 through conduit 52. Separator 55 provides for separation of solid catalyst particles from other materials in the separator 55 in the same manner as described above in relation to separator 45. Solid catalyst particles are withdrawn through conduit 56 and transferred to the first reaction zone in vessel 40.

Materials that are not particulate solids are withdrawn from separator 55 through conduit 58 and may be recovered as product or transferred to the inlet of vessel 60. Vessel 60 provides a third reaction zone which provides for additional contact, if necessary, between isomerization catalyst and the materials introduced through conduit 58. The third reaction zone contains isomerization catalyst which may be added to vessel 60 through conduit 61 connected to the inlet of vessel 60. Conduit 61 provides for the addition of fresh isomerization catalyst to the third reaction zone. The catalyst should be contacted with the other materials in the reaction zone in the manner as described above. The temperature of the third reaction zone may be the same as or lower than the temperature of the second reaction zone, but otherwise, the temperature, pressure and reaction times may be within the limits set forth above.

Solid catalyst particles, unreacted isomerizable olefin compounds and product olefin compounds from the third reaction zone are moved through conduit 62 and transferred to separator 65. Separator 65 provides for the separation of the solid catalyst particles from the product. The solid catalyst particles are withdrawn from separator 65 through conduit 66 and transferred to the second reaction zone in vessel 50. Fluid product may be withdrawn from separator 65 through conduit 68.

The third reaction zone may be unnecessary, in which case, product would be withdrawn from separator 55 through conduit 58, and fresh catalyst would be added to the second (last) reaction zone through conduit 66.

The isomerization reaction of the isomerizable olefin compound to the corresponding product olefin compound occurs in each successive reaction zone unless all of the olefin has already been isomerized. The first reaction zone is usually maintained at a higher temperature in order to provide for rapid conversion. Since the isomerization equilibrium may not favor complete conversion at higher temperatures, further reaction zones provide lower temperature contact between the isomerization catalyst and the materials to be isomerized in order to provide for nearly complete or complete conversion of the isomerizable olefin compound to the desired product olefin compound.

In addition, a further advantage of the invention is realized because of the activity of the particular catalyst for removal of catalyst poisons at higher temperatures. As demonstrated by the following examples, the catalyst has activity to remove or convert the catalyst poisons to harmless compounds and yet retain some of its isomerization activity. This feature of the catalyst is especially pronounced at higher temperatures. Thus, in addition to providing for rapid conversion and complete conversion, the multi-stage process provides a way of removing catalyst poisons so that they do not affect catalyst in later stages of the reaction process. The invention provides for the most economical removal of the catalyst poisons by contacting the stream which may contain the catalyst poison with the already used and therefore less active and less valuable isomerization catalyst.

It is apparent from the embodiment described in FIG. 5 that fresh catalyst added through conduit 61 is first used in the lowest temperature reaction where the least amount of deactivation occurs. The catalyst in the third reaction zone is most active and therefore able to convert the relatively small amounts of isomerizable olefin compound remaining to the corresponding product olefin compound. After the contact in the third reaction zone, the catalyst, which is now less active than fresh catalyst, is transferred to the second reaction zone where the temperature is higher. The higher temperature compensates for the reduced activity of the catalyst. This catalyst, though not as active as fresh catalyst, still provides for significant amounts of isomerization due to the increased temperature in the second reaction zone and the increased amount of reactant isomerizable olefin compound present. The catalyst is then removed from the second reaction zone and transferred to the first reaction zone where it still has useful isomerization activity due to the increased temperature of the first reaction zone and the increased reactant concentration of the isomerizable olefin compound. This staging arrangement for the catalyst provides for the most efficient use of the catalyst and provides for removal of catalyst poisons before they can affect the fresh and most active catalyst.

Figure 6:
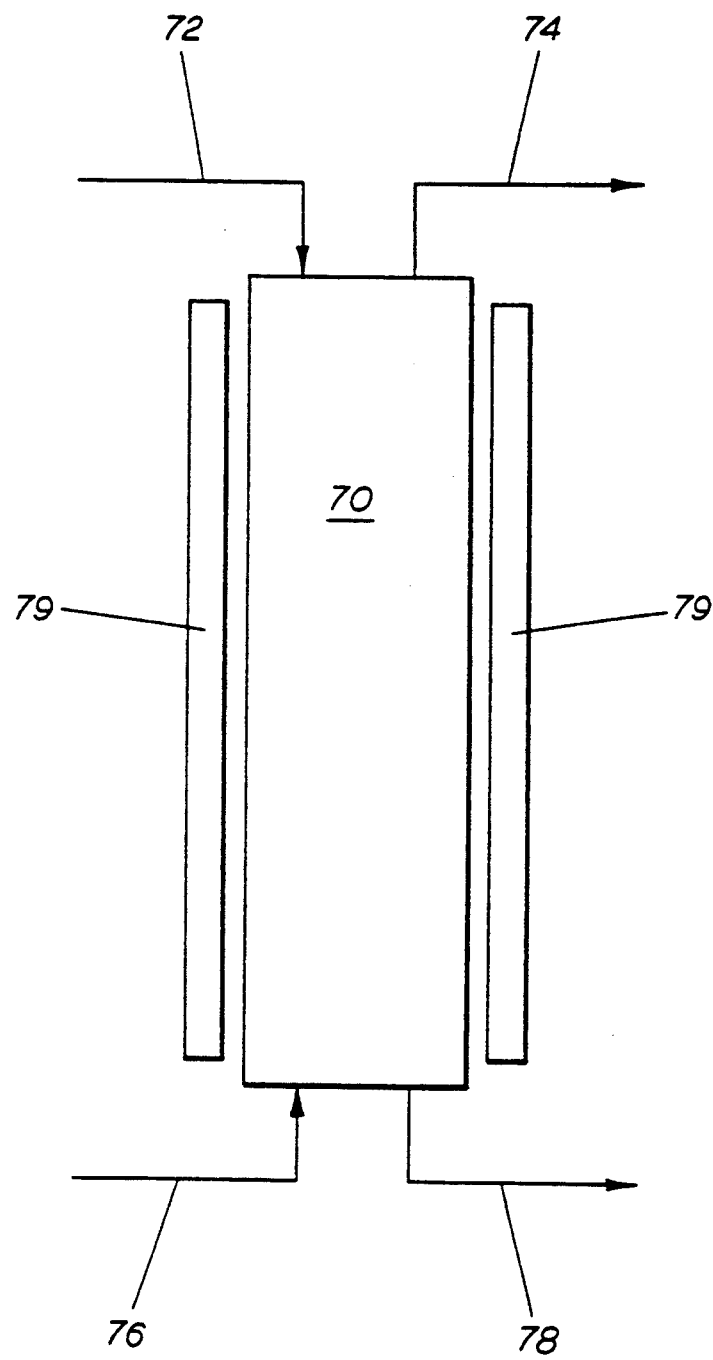
FIG. 6 is a block diagram of a multi-stage process in a single reaction vessel.

Any multi-stage process is within the scope of the invention. It is not necessary to have multiple vessels in order to have a multi-stage process, for example, FIG. 6 depicts an effective multi-stage process occurring in a single reaction vessel 70. Reaction vessel 70 is provided with a conduit 72 for addition of fresh catalyst to the top of the vessel 70. Conduit 76 is connected with vessel 70 at the bottom for addition of a fluid feed stream initially comprising an isomerizable olefin compound. Conduit 78 connected at the bottom of vessel 70 provides for removal of the solid particles of spent catalyst and conduit 74 connected at the top of vessel 70 provides for removal of fluid materials from vessel 70. The top of vessel 70 should be provided with a means for preventing entrainment of solid particles with the fluid withdrawn through conduit 74. The solid catalyst particles introduced to the top of vessel 70 through conduit 72 descend under gravity flow to the bottom of vessel 70 and are then withdrawn through conduit 78. The fluid isomerizable olefin stream added through conduit 76 to the bottom of vessel 70 flows by pressure to the top of vessel 70 and is withdrawn through conduit 74.

The vessel 70 may be provided with a means for removing heat 79 such as a water jacket or any other means of heat exchange so that the bottom of vessel 70 may be maintained at a higher temperature than the top of vessel 70. Preferably, the temperature changes continuously from highest at the bottom to coolest at the top, thereby providing an infinite number of stages. It can be seen in this embodiment that the catalyst is added to the coolest part of the reactor and that the final conversion is also occurring in the coolest part of the reactor at the top of vessel 70. Also, the catalyst which has been deactivated the most is the catalyst used in the warmest part of the reactor which is also the part of the reactor where the feed stream first contacts the catalyst. This provides for the advantageous rapid conversion of isomerizable olefin compounds to product olefin compounds and for removal of catalyst poisons as described above.

Although the description of distinct stages has been in reference to three separate stages, any number of stages may be used to accomplish the beneficial aspects of the invention as long as at least two stages are used. It may also be necessary to add fresh catalyst to some or all of the reaction zones in order to make up for solid catalyst particles which may have become unusable due to breakage or loss through the fluid withdrawal or catalyst movement streams. If the multiple zones differ in temperature, the first reaction zone in the series should be the warmest and the last reaction zone the coolest. In a preferred embodiment the temperature of the first reaction zone ranges between 80° to 130° C. and the temperature of the last reaction zone ranges between 0° to 70° C. preferably 0° to 50°. If there are three reaction zones, the first reaction zone may be maintained at 100° to 130° C., the second reaction zone at 50° to 80° C. and the third reaction zone at 0° to 50° C.

Fresh isomerizable olefin feed should be added to the first reaction zone and sequentially travel through the series of reaction zones until the fluid stream exits from the last reaction zone. Although the fluid stream initially comprised an isomerizable olefin, all of the material in the fluid stream may have been converted to product olefin by the time the fluid stream exits.

Fresh catalyst may be added to each reaction zone at the same time or it may be added to the last reaction zone and travel sequentially through the reaction zones until it exits from the first reaction zone. Fractionation of the fluid streams between reaction zones is also within the scope of the inventive multi-stage process. In such an embodiment, product olefin would be removed between reaction zones so that only isomerizable olefin would be fed to the next reaction zone.

Use of the above described catalyst and multi-stage process to isomerize VNB usually results in nearly complete conversion to ENB and therefore no product purification is necessary. The resulting ENB may be transferred directly to a polymerization process to make EPDM rubber. If for some reason the conversion rates are lower, the ENB may be purified of VNB by known methods such as by distillation.

Conversion percentages herein are determined by subtracting the weight amount of compound remaining after isomerization from the beginning amount of the compound and dividing the result by the beginning amount of the compound. The resulting quotient is multiplied by 100% to express the conversion in percent. Selectivity is determined by dividing the weight amount of material converted into desired product by the total amount of material converted and multiplying the result by 100%.

Particular aspects of the invention may be further understood by reference to the examples below. While these examples are provided to illustrate and describe specific features of the invention, they should not be construed as limitations on the scope of the invention which is more fully described above.

EXAMPLE 1

This example demonstrates a method of preparing a catalyst according to the invention. The following procedures were conducted in a $N_2$ dry-box. Fifteen grams of calcined, 50/100 mesh alumina powder and 1.5 g of fresh-cut sodium (65.2 mg-atom) were placed in a 300 mL 3-neck flask equipped with a stir shaft with a glass paddle, a "Y"-adapter, a hose nipple, a gas addition tube, and a stopper. The flask was subjected to a vacuum for 30 minutes, and then the flask was filled with dry nitrogen. The flask was taken from the dry-box while filled with nitrogen. The contents were stirred, and heated with an electric heating mantle to a skin temperature of 400° C. for 2 hours to form an evenly dispersed mixture of sodium on alumina. Afterwards, the skin temperature was reduced to 150° C., and an activating gas of 5% $O_2$ and 95% $N_2$ was added at 0.07 L/min via the gas addition tube. The activating gas addition continued for 90 min with good stirring. The resulting catalyst was then allowed to cool to room temperature under a $N_2$ atmosphere.

Two grams of the catalyst prepared as noted above were placed all at once into a vessel containing water. There was no indication of gas evolution or any strong exothermic reaction.

EXAMPLE 2

This example demonstrates isomerization of VNB to ENB at low temperatures according to one embodiment of the invention. In a $N_2$ dry-box, 25 g of VNB (208 mmole) and 2 g decane were placed into a 50 mL Erlenmeyer flask equipped with a teflon coated spinbar. Then, 0.5 g of the catalyst prepared according to Example 1 was added, and the mixture was stirred vigorously at room temperature. After 3 hours, the VNB conversion was 99.6% and the selectivity to ENB was 99.7%.

EXAMPLE 3

This example demonstrates isomerization of VNB to ENB at relatively high temperatures according to one embodiment of the invention. Under nitrogen, 50 g of dry VNB (417 mmole) and 5 g of decane, as a GC standard, were placed into a 300 mL round-bottomed flask equipped with a paddle stirrer. The VNB mixture was heated to 120° C., and 1.0 g of catalyst prepared according to Example 1 was added while vigorous stirring was maintained. After 60 minutes, the VNB conversion was 98%, and the selectivity to ENB was 99.7%.

EXAMPLE 4

This example illustrates a high temperature activation of the catalyst. Fifteen grams of alumina powder with a surface area of 90 $m^2/g$ was calcined for one hour at 500° C. under a nitrogen atmosphere. The calcined alumina was then cooled to room temperature and subjected to a vacuum for 30 minutes and thereafter blanketed with nitrogen. 1.5 g of sodium was added to the calcined alumina, and the mixture was heated at a rate of 6° C./min with stirring until a temperature of 400° C. was reached. The stirring of the mixture continued while the temperature of the mixture was held at 400° C. for one hour. After the mixture cooled to a temperature of 150° C., an activating gas comprising 5% $O_2$ and 95% $N_2$ by volume was passed through the mixture for 90 minutes at a rate of 0.07 L/min.

EXAMPLE 5

Figure 2:
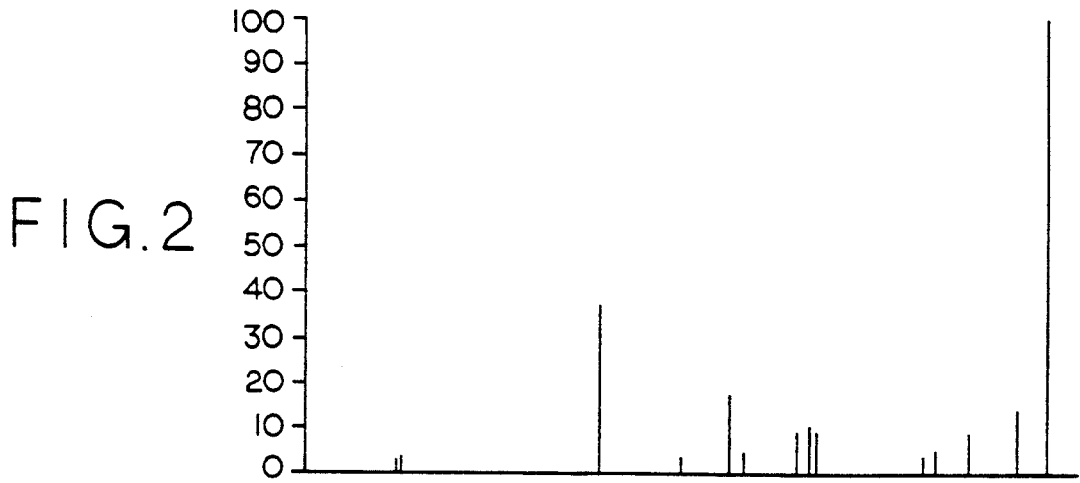
FIG. 2 is an X-ray diffraction pattern for a catalyst made according to the invention.
Figure 3:
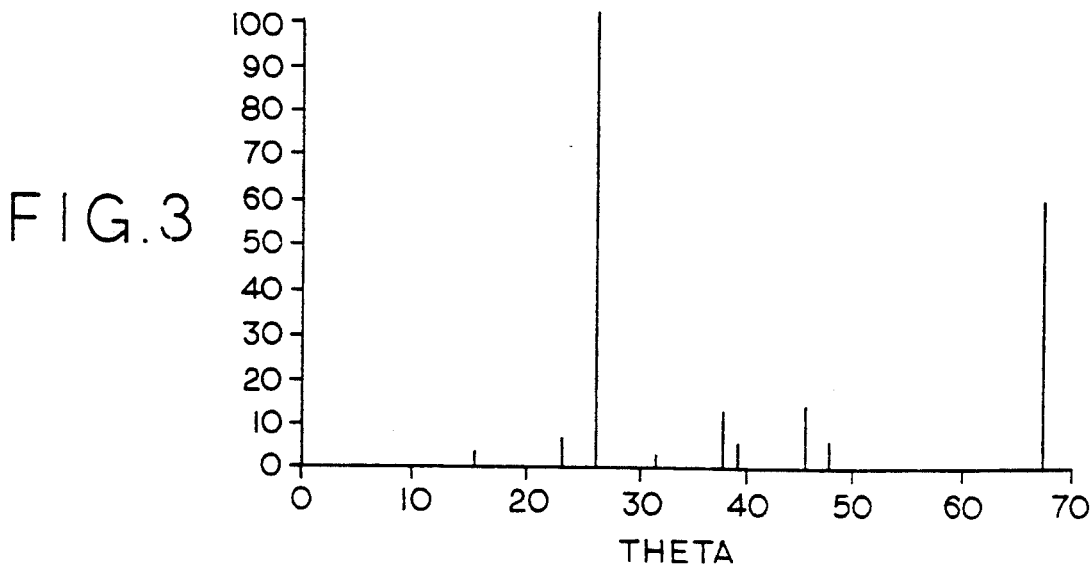
FIG. 3 is an X-ray diffraction pattern for a catalyst made according to the prior art.

X-ray diffraction patterns for three solids were measured and are compared in the FIGS. 1-3. The X-ray diffraction pattern for the raw alumina from Example 4 is represented by FIG. 1. The X-ray diffraction pattern for the sodium catalyst made according to Example 4 is represented at FIG. 2. The X-ray diffraction pattern for a catalyst made according to U.S. Pat. No. 3,928,485 using the same alumina used in Example 4 is represented by FIG. 3. The catalyst made according to U.S. Pat. No. 3,928,485 was prepared as follows.

Fifteen grams of dried alumina and 1.5 g NaOH were ground together, and then mixed under nitrogen for 2 hours at a temperature of 330° C. The temperature was then lowered to 90° C. and 0.83 g of sodium was added to the mixture. Thereafter the mixture was stirred and heated to a temperature of 400° C. Stirring continued for 2 hours while the temperature was maintained at 400° C.

EXAMPLE 6

This example demonstrates isomerization in the presence of an isomerization catalyst poison. 0.25 g of a catalyst made according to Example 1 was stirred at 120° C. with VNB which contained 0.03% cyclopentadiene, a known isomerization catalyst poison. After one hour of stirring, 60% of the VNB had been converted and all of the cyclopentadiene had been converted.

4.0 g of a catalyst prepared in accordance with Example 1 was stirred at 25° C. with 200 g VNB which contained 0.06% cyclopentadiene. After one hour of stirring, the cyclopentadiene concentration was reduced to 0.03% and the VNB conversion was 10%. This example shows that the negative effects of cyclopentadiene are less pronounced at higher temperature isomerization. The example also shows that the cyclopentadiene may be removed faster at higher temperature.

EXAMPLE 7

This example demonstrates the extra safety of using an activated catalyst. An alumina with a surface area of 210 $m^2/g$ was calcined at 400° C. for one hour and then held under a vacuum at 200° C. for one hour. 4.5 g of sodium metal was added to two separate 30 g portions of the calcined alumina. The resulting mixtures were stirred at 210° C. for one hour after which the temperature was increased to 410° C. and mixing continued for one more hour. The mixtures were then cooled to room temperature. The first portion was contacted with water resulting in a very violent exothermic reaction.

The second portion was first treated with an activating gas of 5 volume % $O_2$ and 95 volume % $N_2$. The second activated catalyst portion was treated with water in a manner similar to the first portion but only a very mild exothermic reaction resulted.

EXAMPLE 8

This example demonstrates that the activated catalyst has superior resistance to catalyst poisons. The activating gas treated catalyst prepared according to Example 7 was stirred for one hour at 25° C. in a solution of VNB with 0.06% cyclopentadiene. The amount of catalyst used was 4 wt % of the total weight of the solution and the conversion of VNB was 40%. When the same amount of catalyst prepared according to Example 7 without the activating gas treatment was similarly contacted with the same solution of VNB with cyclopentadiene, the conversion of VNB was 25%.

EXAMPLE 9

This example demonstrates that the activated catalyst has an activity equivalent to a more dangerous non-activated catalyst. The activated and non-activated catalysts prepared in Example 7 were contacted with purified VNB. For each contact, 2 wt % of catalyst was used based on the weight of purified VNB. The conversions after one hour were 52% for the activated catalyst and 58% for the non-activated catalyst.

EXAMPLE 10

This example demonstrates the reactivity of sodium on alumina with water. Sodium materials are difficult to handle because of their explosive reactivity with air and water and therefore require special care in shipping and processing. Twenty grams of alumina powder and 3 grams of Na (0.13 gram-atom) were mixed at 300° C. for 1 hour under a nitrogen atmosphere. The mixture was cooled, and then carefully mixed with kerosene. Addition of water to this slurry set off an exothermic reaction that was accompanied by evolution of large quantities of gas from the mixture.

EXAMPLE 11

This example demonstrates various catalysts prepared on alumina with different surface areas. For each catalyst prepared, the alumina was calcined at 400° C. in air for 1 hour. Thereafter, the air was removed and the temperature reduced to 200° C. The alumina was maintained under vacuum at 200° C. for 1 hour.

Thirty grams of the alumina prepared as noted above were then mixed with 4.5 g of sodium under a nitrogen atmosphere at 210° C. The mixing continued for 1 hour after which the temperature was increased to 410° C. Mixing continued at 410° C. for 1 more hour under the nitrogen atmosphere resulting in an evenly distributed mixture of sodium on alumina.

The mixture was cooled to room temperature (25° C.) and then contacted with a gas consisting of 5% oxygen and 95% nitrogen. The gas flow rate was maintained at 126 mL/min while the mixture was continuously stirred for 152 minutes.

VNB was contacted with 2 wt % of the catalyst prepared as noted above. The VNB/catalyst solution was stirred at room temperature for 1 hour. A sample of the resulting solution was taken and the conversion of VNB was measured.

The 11-A alumina was supplied as AL-0171P by Engelhard and had a surface area of 210 $m^2/g$. The VNB conversion for 11-A was 55%. The 11-B alumina was supplied by Engelhard designated AL-1040P and had a surface area of 180 $m^2/g$. The VNB conversion for 11-B was 99.8%. The 11-C alumina was supplied by Engelhard as AL-3916P and had a surface area of 155 $m^2/g$. The conversion level for 11-C was 68%.

As can be seen from the conversion levels above, the alumina with a surface area of about 180 $m^2/g$ is the preferred support material. Currently, aluminas with surface areas of about 180 $m^2/g$ are preferred. Both Engelhard AL 1040P and AL 3970P are preferred starting aluminas.

The examples set forth above illustrate aspects of the invention and are not limitations on the scope of the invention which is set forth in the claims below. Many other variations and modifications may be made to the process and catalyst described above without departing from the concept of the present invention. Accordingly, it should be clearly understood that the methods depicted in the accompanying figures and referred to in the foregoing description are illustrative only and are not intended as limitations on the scope of the invention.

That which is claimed is:

1. A process for isomerizing an alkenyl bridged ring compound comprising:
    (a) passing a fluid stream initially comprising an alkenyl bridged ring compound sequentially through a series of reaction zones from a first reaction zone to a last reaction zone; and
    (b) contacting the fluid stream with an isomerization catalyst in each reaction zone;
    wherein: (i) the isomerization catalyst comprises an oxygen treated mixture of an alkali metal supported on a calcined support material consisting essentially of alumina, (ii) the isomerization catalyst is transferred sequentially to all reaction zones from the last reaction zone to the first reaction zone, and (iii) the temperature of the first reaction zone ranges between 80° to 130° C. and the temperature of the last reaction zone ranges between 0° to 70° C.

2. A process in accordance with claim 1 wherein the fluid stream is passed through a series of three sequential reaction zones.

3. A process in accordance with claim 2 wherein the alkali metal is sodium.

4. A process in accordance with claim 3 wherein the fluid stream further initially comprises a catalyst poison prior to introduction to the first reaction zone.

5. A multi-stage process for isomerizing a stream comprising an isomerizable olefin which comprises:
    (a) introducing a stream comprising an isomerizable olefin to a first reaction zone and contacting the stream with an isomerization catalyst, whereby some of the isomerizable olefin is converted to product olefin;
    (b) removing from the first reaction zone a first outlet fluid stream comprising unconverted isomerizable olefin;
    (c) removing from the first reaction zone a first outlet catalyst stream comprising isomerization catalyst from the first reaction zone;
    (d) introducing the first outlet fluid stream to a second reaction zone and contacting the first outlet fluid stream with an isomerization catalyst therein whereby some of the isomerizable olefin is converted to product olefin;
    (e) removing from the second reaction zone a second outlet fluid stream;

(f) removing from the second reaction zone a second outlet catalyst stream comprising isomerization catalyst from the second reaction zone; and (g) introducing the second outlet catalyst stream to the first reaction zone; wherein (i) the isomerizable olefin is an alkenyl bridged ring compound, (ii) the isomerization catalyst comprises an alkali metal dispersed on a calcined support material (iii) the isomerization catalyst is treated with an oxygen containing gas before contact with the isomerizable olefin, and (iv) the temperature of the first reaction zone ranges between 80° to 130° C. and the temperature of the second reaction zone ranges from 0° to 70° C.

6. A process in accordance with claim 5 wherein the stream comprising an isomerizable olefin further comprises a catalyst poison prior to introduction to the first reaction zone.

7. A multi-stage process for isomerizing a stream comprising an isomerizable olefin which comprises:

(a) introducing a stream comprising an isomerizable olefin to a first reaction zone and contacting the stream with an isomerization catalyst, whereby some of the isomerizable olefin is converted to product olefin;

(b) removing from the first reaction zone a first outlet fluid stream comprising unconverted isomerizable olefin;

(c) removing from the first reaction zone a first outlet catalyst stream comprising isomerization catalyst from the first reaction zone;

(d) introducing the first outlet fluid stream to a second reaction zone and contacting the first outlet fluid stream with an isomerization catalyst therein whereby some of the isomerizable olefin is converted to product olefin;

(e) removing from the second reaction zone a second outlet fluid stream;

(f) removing from the second reaction zone a second outlet catalyst stream comprising isomerization catalyst from the second reaction zone;

(g) introducing the second outlet catalyst stream to the first reaction zone;

(h) introducing the second outlet fluid stream to a third reaction zone and contacting the second outlet fluid stream with an isomerization catalyst therein;

(i) removing a third outlet fluid stream from the third reaction zone;

(j) removing a third outlet catalyst stream comprising isomerization catalyst from the third isomerization zone; and (k) introducing the third outlet catalyst stream to the second reaction zone;

wherein (1) the isomerizable olefin is an alkenyl bridged ring compound, (2) the isomerization catalyst comprises sodium dispersed on a calcined support material consisting essentially of alumina, (3) the isomerization catalyst is treated with an oxygen containing gas before contact with the isomerizable olefin, and (4) the temperature of the first reaction zone is 100° to 130° C., the temperature of the second reaction zone is 50° to 80° C. and the temperature of the third reaction zone is 0° to 50° C.

* * * * *